US009458990B2

(12) United States Patent
Mullani

(10) Patent No.: US 9,458,990 B2
(45) Date of Patent: Oct. 4, 2016

(54) DERMOSCOPY ILLUMINATION DEVICE WITH SELECTIVE POLARIZATION AND ORANGE LIGHT FOR ENHANCED VIEWING OF PIGMENTED TISSUE

(71) Applicant: 3Gen, Inc., San Juan Capistrano, CA (US)

(72) Inventor: Nizar Mullani, Sugar Land, TX (US)

(73) Assignee: 3Gen, Inc., San Juan Capistrano, CA (US)

( * ) Notice: Subject to any disclaimer, the term of this patent is extended or adjusted under 35 U.S.C. 154(b) by 0 days.

(21) Appl. No.: 13/957,229

(22) Filed: Aug. 1, 2013

(65) Prior Publication Data

US 2015/0036311 A1 Feb. 5, 2015

(51) Int. Cl.
*F21K 99/00* (2016.01)
*F21V 9/14* (2006.01)
*A61B 5/00* (2006.01)
*F21W 131/20* (2006.01)

(52) U.S. Cl.
CPC ............... *F21V 9/14* (2013.01); *A61B 5/0059* (2013.01); *A61B 5/441* (2013.01); *F21K 9/00* (2013.01); *F21W 2131/20* (2013.01)

(58) Field of Classification Search
CPC .......... F21V 9/00; F21V 9/14; F21S 48/114; A61B 5/441; A61B 5/0059; F21W 2131/20; F21K 9/00
USPC ........... 362/19, 369, 356, 445–448, 39, 230, 362/231, 572, 804, 140, 249.05; 600/410, 600/425, 476–478
See application file for complete search history.

(56) References Cited

U.S. PATENT DOCUMENTS

| 2,120,365 | A | 6/1938 | Kriebel |
| 2,866,375 | A | 12/1958 | Wells et al. |
| 2,947,212 | A | 8/1960 | Woods |
| 3,062,087 | A | 11/1962 | Zandman et al. |

(Continued)

FOREIGN PATENT DOCUMENTS

| IT | 01300568 | 10/1999 |
| JP | 04214523 A | 12/1990 |

OTHER PUBLICATIONS

Google Search—Orange light wavelength range, 2 pages search resutls, multiple sources.*

(Continued)

*Primary Examiner* — Anh Mai
*Assistant Examiner* — Arman B Fallahkhair
(74) *Attorney, Agent, or Firm* — Stetina Brunda Garred & Brucker

(57) ABSTRACT

An illumination device used in dermoscopy for enhanced imaging and illumination of the skin for medical examination and treatment. An array of LEDs encircle a magnifying lens assembly. One set of surrounding LEDs provides cross-polarized white light to aid in canceling the reflected light from the skin and creating less glare. Another set of surrounding LEDs provides non-polarized white light for traditional immersion fluid dermoscopy or for non-polarized viewing of the skin. A third set of surrounding LEDs provides polarized colored light, wherein the wavelength color is selected at a color wavelength that maximizes the viewing of skin pigment regions which is important for early detection of skin cancers and other skin diseases. In one embodiment, the colored LEDs comprise orange light at a wavelength in the range of 581 nm to 600 nm wavelengths.

27 Claims, 9 Drawing Sheets

(56) References Cited

U.S. PATENT DOCUMENTS

| | | | |
|---|---|---|---|
| 3,711,182 | A | 1/1973 | Jasgur |
| 4,007,979 | A | 2/1977 | Coblitz |
| 4,398,541 | A | 8/1983 | Pugliese |
| 4,773,097 | A | 9/1988 | Suzaki et al. |
| 4,846,184 | A | 7/1989 | Comment et al. |
| 4,957,368 | A | 9/1990 | Smith |
| 4,998,818 | A | 3/1991 | Kugler et al. |
| 5,146,923 | A | 9/1992 | Dhawan |
| 5,198,875 | A | 3/1993 | Bazin et al. |
| 5,343,536 | A | 8/1994 | Groh |
| 5,363,854 | A | 11/1994 | Martens et al. |
| 5,690,417 | A | 11/1997 | Polidor et al. |
| 5,742,392 | A | 4/1998 | Anderson et al. |
| 5,760,407 | A * | 6/1998 | Margosiak et al. ........ 250/461.2 |
| 6,032,071 | A * | 2/2000 | Binder ................. A61B 5/0059 356/369 |
| 6,069,565 | A | 5/2000 | Stern et al. |
| 6,081,612 | A | 6/2000 | Gutkowicz-Krusin et al. |
| 6,118,476 | A | 9/2000 | Morito et al. |
| 6,207,136 | B1 | 3/2001 | Matsuoka |
| 6,384,988 | B1 | 5/2002 | Muller et al. |
| 6,483,247 | B2 | 11/2002 | Edwards et al. |
| 6,587,711 | B1 | 7/2003 | Alfano et al. |
| 6,842,635 | B1 * | 1/2005 | Parker .......................... 600/323 |
| 7,004,599 | B2 * | 2/2006 | Mullani ............... G02B 27/281 359/488.01 |
| 7,006,223 | B2 | 2/2006 | Mullani |
| 7,027,153 | B2 | 4/2006 | Mullani |
| 7,167,243 | B2 | 1/2007 | Mullani |
| 7,167,244 | B2 | 1/2007 | Mullani |
| 7,400,918 | B2 * | 7/2008 | Parker et al. ................. 600/323 |
| 7,621,653 | B2 * | 11/2009 | Hendrie ........................ 362/231 |
| 7,874,698 | B2 | 1/2011 | Mullani |
| 7,986,987 | B2 * | 7/2011 | Bazin .................... A61B 5/448 600/407 |
| 8,496,695 | B2 | 7/2013 | Kang et al. |
| 8,588,605 | B2 | 11/2013 | Harris |
| 2003/0026110 | A1 | 2/2003 | Satoh et al. |
| 2003/0045799 | A1 | 3/2003 | Bazin et al. |
| 2004/0062056 | A1 | 4/2004 | Heine et al. |
| 2008/0015663 | A1 | 1/2008 | Mullani |
| 2008/0065176 | A1 * | 3/2008 | Zhang et al. .................. 607/88 |
| 2009/0093761 | A1 * | 4/2009 | Sliwa et al. ................. 604/116 |
| 2011/0270200 | A1 * | 11/2011 | Edgar et al. ................. 604/290 |
| 2011/0304705 | A1 | 12/2011 | Kantor et al. |
| 2014/0243685 | A1 | 8/2014 | Patwardhan et al. |

OTHER PUBLICATIONS

Keshen R. Mathura et al., "Comparison of OPS imaging and conventional capillary microscopy to study the human microcirculation," The American Physiological Society, vol. 91, p. 74-78, 2001 (5 pages).

Unknown (Internet Literature), www.syrisscientific.com, "Technical", 1 page (Unknown publication date).

(Brochure) 3gen, LLC., "First in Pocket Epiluminescence Microscopy," 1 page, Mar. 15, 2001 (Estimated publication date).

(Brochure) 3gen, LLC., "3gen the Beauty of Evolutionary Innovation," 3 pages (trifold), Feb. 15, 2002 (Estimated publication date) (6 pages).

Pan, Yan et al., "Polarized and Nonpolarized Dermoscopy the Explanation for the Observed Differences", American Medical Society, (Reprinted) Arch Dermatol, vol. 144 (No. 6), Jun. 2008 (2 pages).

Dhawan, Atam P. et al., "Multispectral Optical Imaging of Skin-Lesions for Detection of Malignant Melanomas", 31st Annual International Conference of the IEEE EMBS, Minneapolis, MN, USA Sep. 2-6, 2009, p. 5352-5355, 2009, (4 pages).

Arrazola, Peter et al., "Dermlite II: An Innovative Portable Instrument for Dermoscopy Without the Need of Immersion Fluids", Skin Med, LE JACQ Mar.-Apr. 2005; 10: p. 78-83 (6 pages).

Garcia-Uribe, Alejandro et al., "In-vivo characterization of optical properties of pigmented skin lesions including melanoma using oblique incidence diffuse reflectance spectrometry", Journal of Biomedical Optics, vol. 16 (2), p. 020501-1-020501-3, Feb. 2011 (3 pages).

(Flyer), VISOMED, "MicroDERM Luminis The hand-held demoscope with daylight optics", Visiomed AG 2009, (2 pages).

(Instruction Manual—English Portion) "DermLite DL1", 3Gen, LLC., 2011 (1 page).

(Instruction Manual—English Portion) "DermLite II Fluid", 3Gen, LLC., 2006 (1 page).

(Instruction Manual—English Portion) "DermLite II Hybrid m", 3Gen, LLC., 2009 (1 page).

(Instruction Manual—English Portion) "DermLite II PRO HR", 3Gen, LLC., 2008 (1 page).

(Instruction Manual—English Portion) "DermLite II Pro", 3Gen, LLC., 2007 (1 page).

(Instruction Manual—English Portion) "DermLite DL3", 3Gen, LLC., 2009 (1 page).

(Instruction Manual—English Portion) "DermLite carbon", 3Gen, LLC., 2003-2008 (Estimated publication date) (1 page).

(Instruction Manual—English Portion) "DermLite cam Dermoscopy Camera", 3Gen, LLC., 2001-2013 (Estimated publication date) (1 page).

(Instruction Manual—English Portion) "DermLite DL100", 3Gen, LLC., 2003-2008 (Estimated publication date) (1 page).

(Instruction Manual—English Portion) "DermLite II Multispectral", 3Gen, LLC., 2004 (1 page).

(Instruction Manual—English Portion) "Lumio DermLite", 3Gen, LLC., 2007 (1 page).

(Instruction Manual—English Portion) "DermLite Foto Quickstart Guide", 3Gen, LLC., 2009 (1 page).

Barun, Vladimir V., "Absorption spectra and light penetration depth of normal and pathologically altered human skin", ResearchGate, (Website) Journal of Applied Spectroscopy, vol. 74 (No. 3), Mar. 2007 (11 pages). https://www.researchgate.net/publication/225598882.

* cited by examiner

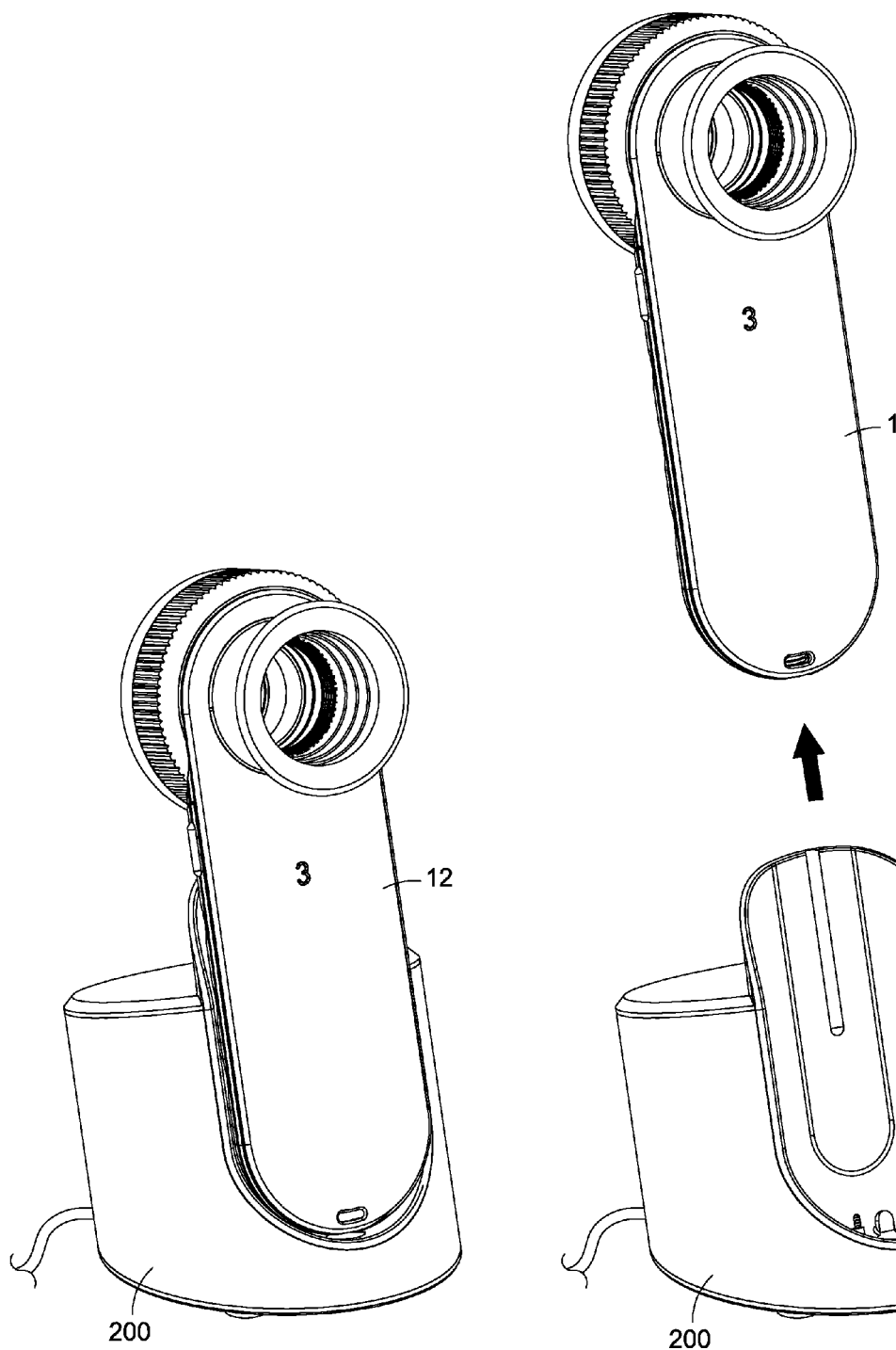

DERMOSCOPY ILLUMINATION DEVICE WITH SELECTIVE POLARIZATION AND ORANGE LIGHT FOR ENHANCED VIEWING OF PIGMENTED TISSUE

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Field of the Invention

The present invention relates generally to an illumination device used in dermoscopy. More particularly, the invention comprises an improved apparatus for enhanced imaging and illumination of the skin for medical examination and treatment.

2. Background

When using surface illumination to view human skin in medical examination, a great deal of surface light is reflected from the top layer of skin. Hand held dermoscopy devices that use light along with magnification can utilize polarizers or liquid-glass interface to reduce surface reflection and see deeper in to the skin. Dermoscopy apparatuses that employ light polarization to aid in viewing human skin surfaces and deeper tissue and structures of the skin are known and described U.S. Pat. Nos. 7,006,223 and 7,167,243 both issued to Mullani, the substance of each of which is incorporated herein by reference. In addition, a dermoscopy device identified as Dermlite® DL3 device is manufactured and marketed by 3Gen, Inc. of San Juan Capistrano. In the Dermlite® DL3 hand held device, a series of light emitting diodes ("LEDs") are concentrically positioned around a magnifying lens to assist in lighting of a magnified image. The device includes two sets of white light LEDs that can be activated independently; one set of twenty one (21) LEDs provides reduced glare cross-polarized light to aid in canceling the reflected light from the skin, whereas the other set of seven (7) LEDs provides non-polarized light for traditional immersion fluid dermoscopy or for simply employing non-polarized light. Both sets of LEDs can be operated independently or at the same time. Users of the Dermlite® DL3 can toggle between polarized and non-polarized light to provide an enhanced perspective of skin surface and lesions.

It is also well known that different colored light penetrates to different depths in human skin tissue. Specific color wavelengths are absorbed differently by different components of the skin tissue. Such use of colored LEDs in a dermatoscope is described in U.S. Pat. Nos. 7,027,153 and 7,167,244 both issued to Mullani, the substance of each of which is incorporated herein by reference. The previously identified references disclose the combined use of white LEDs, UV/blue LEDs (405 nm), green/yellow LEDs (565 nm) and orange/red (630 nm). Alternatively, the 7,027,153 and 7,167,244 references suggest the use of LEDs with 480 nm, 580 nm and 660 nm wavelengths. In addition, a dermoscopy device identified as Dermlite® II Multispectral dermoscopy device manufactured and marketed by 3Gen, Inc. of San Juan Capistrano, Calif. provides four sets LED's comprising white, blue light (470 nm) for surface pigmentation, yellow light (580 nm) for superficial vascularity viewing, and red light (660 nm) for viewing of pigmentation and vascularity with the deeper-penetrating red light frequency.

In related medical examination procedures, such as for viewing structures on the surface and beneath the skin, a further way to introduce more light in to the skin is to use side-transillumination techniques whereby the light source is caused to be in direct contact with the skin to transfer light directly into the skin. One such technique is known and taught in U.S. Pat. No. 5,146,923 issued to Dhawan, the substance of which is incorporated herein by reference. A combination of surface illumination, epiluminescence and transillumination apparatus and method is demonstrated in the Nevoscope™ product sold manufactured by Translite LLC. of Sugar Land, Tex. Another known apparatus and method of viewing vein structures beneath the skin employs the use of transillumination as described in U.S. Pat. No. 7,874,698 issued to Mullani the substance of which is incorporated herein by reference. U.S. Pat. No. 7,874,698 issued to Mullani describes the use of orange light between 580 and 620 nm for transillumination imaging of deeper blood vessels in skin tissue. However, the technology of transillumination is different than imaging skin with direct surface light. In transillumination, the light is directed into the skin by direct contact with the skin.

With respect to Dermatoscopes that use white light to image the skin, white light has a range of colors from Blue to Red. As such, the skin can be visualized up to 3 mm deep depending on the 'color' of the white light. White light used in known dermatoscopes are usually generated by white LEDs and unlike halogen bulb light, the light from these LEDs comprise a great deal of blue light in the spectrum of white light. This bluish tint to the white light makes the dermatoscope more sensitive to the top 1 mm of skin. When using the blue tinted white light in dermatoscopes, it is difficult to see the pigmentation structures in the deeply pigmented areas that are deep. For purposes of early skin cancer detection, viewing pigmentation structures is important for diagnosing cancerous lesions that may be hidden from view at a deeper depth when using blue tinted white light.

To aid in the early detection of skin cancers, the viewing of deeper structures of the skin in close proximity of the skin without the need to contact the skin directly with a light source, or penetrate the skin surface is beneficial for examination, diagnosis and treatment. As described above, polarized white light and colored lights for surface illumination is known. Also, the use of colors in the orange range spectrum is known with respect to translliumiation devices for viewing vein structures. However, there is a great need in the art for a dermoscopy device that can illuminate the skin with white light and/or light in a color range that is adapted to provide a more advantageous viewing of the skin and sub-surface skin structures to enable a more enhanced viewing of pigments and lesions found in the skin that will aid in a visual early detection of various types of skin cancer.

BRIEF SUMMARY

The present invention relates to an epiluminescence microscopy device designed to view skin lesions with high magnification and clarity with a plurality of sets of LEDs (light emitting diodes) that can be activated independently. An array of LEDs encircle a magnifying lens assembly. One set of surrounding LEDs provides cross-polarized light to aid in canceling the reflected light from the skin and creating less glare. Another set of surrounding LEDs provides nonpolarized light for traditional immersion fluid dermoscopy or for non-polarized viewing of the skin. A third set of surrounding LEDs provides polarized colored light, wherein the wavelength color is selected at a color wavelength that maximizes the viewing of skin pigment regions which is important for early detection of skin cancers and other skin diseases. The present invention discloses the range of colored LEDs in the orange portion of the visible spectrum, namely at 581 nm to 600 nm wavelengths.

The device of the present invention includes, among other features, a high quality multi-element, 25 mm, 10× lens that provides color correction and reduced image distortion to produces an image rich surface detail. To facilitate the use of immersion fluids, and allow for fixed digital imaging, the unit is equipped with a retractable faceplate spacer.

The present invention demonstrates that the use of orange light in the specified range as described herein enhances the ability of white light LED based dermatoscopes for imaging deeper pigmentation or blood vessels. The present invention provides for the independent use of cross-polarized white light that can be enhanced with cross-polarized orange light. Alternatively the cross-polarized orange light or white light each can be used independently. The device of the present invention includes the ability to toggle between several modes of operation so that the viewer can toggle between images to provide an enhanced perspective of the skin to a doctor, researcher or healthcare professional. The device of the present invention also provides that the cross polarized orange light can also be used with non-polarized light to enhance the imaging of deeper pigmentation when using a glass-liquid interface and white light.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 11 shows the device of the present invention in a charging assembly; and

FIG. 12 shows the device of the present invention being removed from the charging assembly.

DETAILED DESCRIPTION

Figure 1:
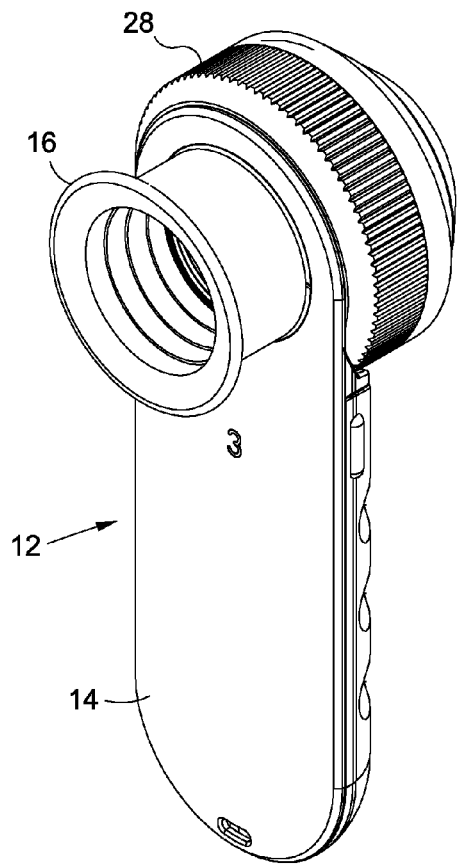
FIG. 1 is a is a top perspective view of the device of the present invention.

It is generally known that light is highly absorbed by the pigmentation in skin lesions for the central part of the visible spectrum from 500 to 570 nm. This high absorption is a problem with visualizing deep pigmented areas because the light gets blocked or absorbed superficially. The absorption of light in pigmentation for the frequencies above 570 nm decreases and this light can be used to see into deeply pigmented areas better.

Surface light falling on human skin in the visible spectrum can include a range of colors with Blue light (450-500 nm) penetrating the shortest distance in skin tissue. Blue light is known to be highly absorbed in pigmentation and blood and as such its depth is limited to less than 1 mm. Green light (500-550 nm) penetrates slightly deeper than blue light and is highly absorbed by hemoglobin in the blood. Yellow-orange light (560-610 nm) light penetrates between 1 and 2 mm depth in skin tissue, while red color light (620-670 nm) penetrates deepest (between 2 and 3 mm).

The present invention demonstrates the use of orange light on skin, with the imaging depth into the skin is between 1 and 2 mm below the surface. Unlike blue light, which is more absorbed by pigmentation and blood up to a depth of 1 mm, the orange light is better for imaging pigmentation and blood vessels between 1 and 2 mm below skin. Pigmented lesions can vary in depth from very superficial to deeper than 2 mm.

The imaging of the deeply pigmented lesions and deeper blood vessels can be enhanced by the addition of an orange light (581 nm to 560 nm) when added to, or compared against the blue tinted white LED light in dermatoscopes. Also, the present invention demonstrates the polarization of the orange light so that it can penetrate deeper in tissue and include less reflected glare as compared to the conventional surface light.

The two major absorptions of light in human skin are from melanin and hemoglobin in the blood. Below is a chart (shown in Table 1) demonstrates the coefficient data for Melanin and Hemoglobin and the depth of penetration of light for the identified specific light wavelengths. These values are approximations of know data graphed in the following publications:

V. Venugopalan slides, http://www.osa.org/meetings/archives/2004/BIOMED/Program/#educ. The graphed data in Table 1 includes different values for oxygenated and deoxygenated blood, and the below chart takes the average of the two values. The light penetration depth was disclosed in the article: A Bashkatov et al. J PHys D Appl Phys 38:2543-2555 (2005).

TABLE 1

|  | 480 nm | 585 nm |
| --- | --- | --- |
| Melanin Absorption Coefficient/cm | 1000 | 500 |
| Hemoglobin Absorption Coefficient/cm | 100 | 300 |
| Light Penetration Depth (mm) | 0.75 | 1.5 |

The data in the chart demonstrates that the melanin absorption data for white light has a peak at around 480 nm and a broad peak at around 525 nm. The broad peak can vary due to the types of chemicals used to convert the blue light to white light. The orange light supplied by the device of the present invention penetrates deeper than the blue color of the white light with the orange light being absorbed to a lesser degree than the blue color in melanin.

The present invention demonstrates that the use of orange light in the range of 581-600 nm used in dermatoscopes enhances the ability of the user to view deeper into the skin and into pigmentation and blood vessels. Visualizing pigmentation becomes more difficult at around 700 nm due to the fact that the pigmentation becomes almost transparent for deep red to near infrared light. As such, the optimum light frequency for detection of pigmentation and deeper penetration includes the range of 581 to 600 nm.

In this regard, the orange light enhancement is especially adapted for viewing pigmented skin, when used alone or combined with the white light of the other LEDs. Because many cancerous lesions involve pigmentation, the device of the present invention provides enhanced viewing of the pigmented regions along with enhanced viewing of the perimeter of the pigmented regions which can be revealing in examination and diagnosis. Another effect of the orange light is that it is absorbed by hemoglobin in the blood. Malignant lesions tend to have higher blood volume around them due to the growth of new blood vessels. As such, abnormal vein activity surrounding a lesion may be identified with increased viewing depth and interaction of the orange light with hemoglobin.

The present invention provides independent use of cross-polarized white light that can be enhanced with cross-polarized orange light. Alternatively the cross-polarized light can be used independently. As a further alternative, the device of the present invention includes the ability to toggle between several modes of operation so that the viewer can toggle between images for an enhanced perspective of the skin. The device of the present invention provides that the cross polarized orange light can also be used with non-polarized light to enhance the imaging of deeper pigmentation when using a glass-liquid interface and white light. Although the present invention demonstrates that the orange light is polarized, it is contemplated and within the scope of the present invention that the orange light can be non-polarized or simply polarized.

Also, although the present invention identifies specific ranges or specific wavelengths for the LEDs used in the invention, the exact color of the orange light may vary slightly depending on the commercial availability of the color of the LEDs. Also, a specific number of LEDs in various combinations are provided, the number of white and orange LEDs can be varied depending on the brightness of each of the LEDs or other factors.

Figure 2:
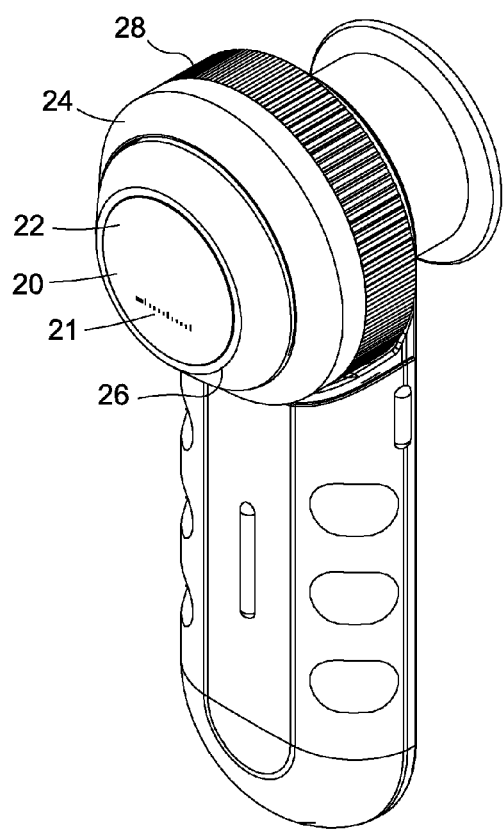
FIG. 2 is a bottom perspective view of the device of the present invention.

Referring collectively to FIGS. 1 and 2 the illumination device of the present invention 12 is shown with a housing 14 that is adapted to be hand held and to encase, among other things, a battery (not shown) lighting sources (not shown) and magnification lenses (not shown). While the disclosure of the present invention shows a hand held, battery powered device, it is contemplated by the present invention that the components of the invention that provide the beneficial illumination for skin examination could be could be incorporated into other types of diagnostic devices, such as fiber optic hand pieces or incorporated into surgical lighting or other types of examination lighting. Preferably, the housing 14, and other internal sub-assembly pieces of the structure of the device of the present invention is formed of assembled pieces of injection molded polycarbonate and polyurethane. It will be recognized by one skilled in the art that the housing 14 can be formed form other suitable rigid lightweight material, including, but not limited to plastic, composite materials, fiberglass, aluminum, PVC, acetate and or lexan. The housing 14 of the device is adapted to be cleaned and disinfected as is necessary.

An eyepiece 16 is attached to the housing 14 to allow a user to view central lenses (not shown) that are incorporated into the housing 14. The annular eyepiece 16 is in visual communication with a proximal viewing port 20, that includes a glass faceplate 22 comprised attached to a spacer (not shown) and held in place by a capture 24, creating a line of sight form the eyepiece 16 through the housing 14 to the viewing port 20, through glass faceplate 22. The view corridor through ports 16 and 20 allows a user to view with the skin with a naked eye to view subject skin placed below proximal viewing port 20. The housing 14 includes a retaining ring 24 that when in a secured position holds a spacer 26 in place, and the spacer 26 face incorporations a glass faceplate 22. A focus dial 28 is provided for adjusting position of spacer by extending or retracting the same to adjust the focal distance to the object or tissue to be viewed (not shown).

Figure 3:
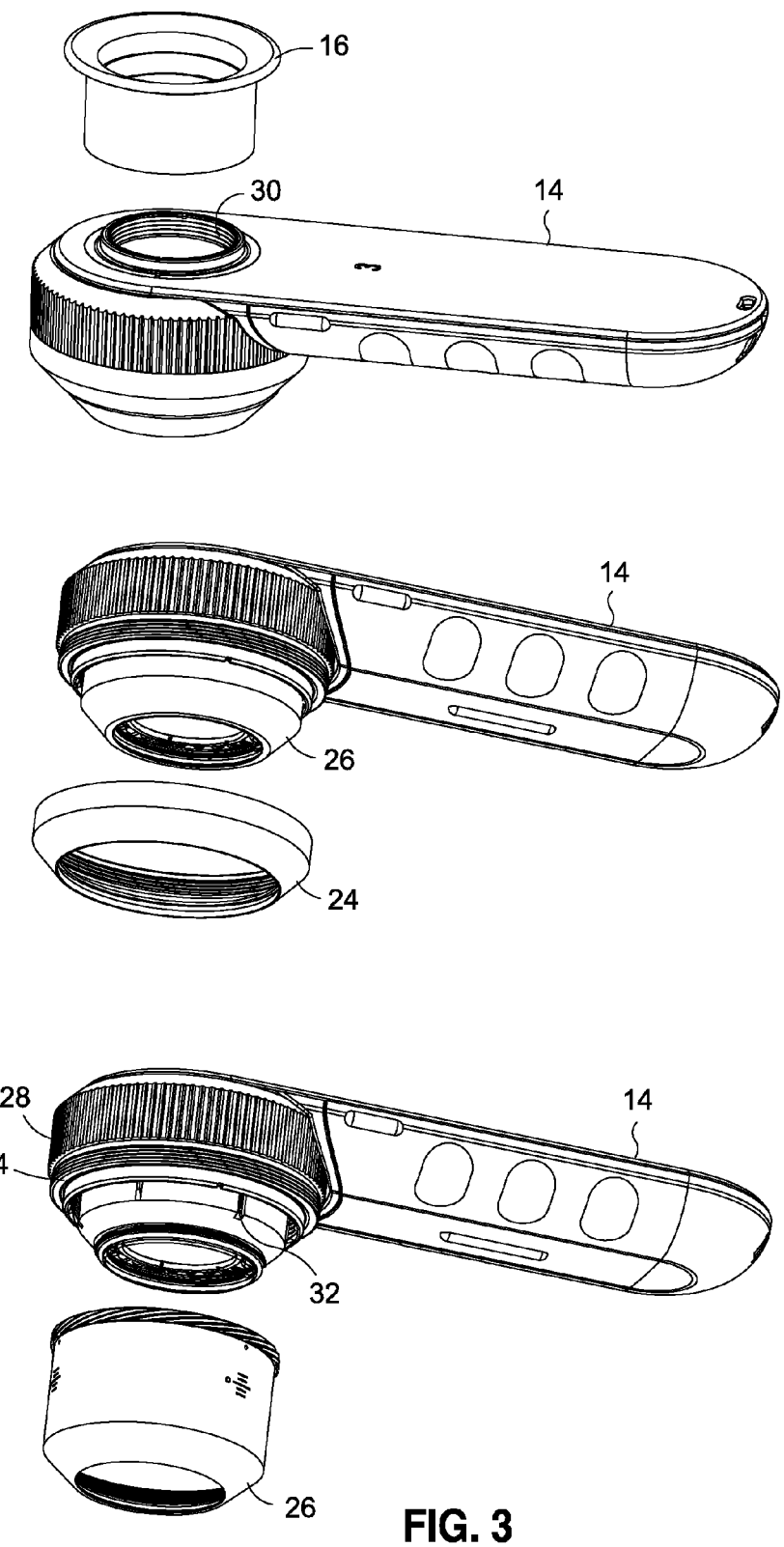
FIG. 3 is a composite view of the device of the present invention demonstrating the removable and retractable features of the device of the present invention.

Referring particularly to FIG. 3, a composite drawing demonstrates the various removable components of the device of the present invention. The eyepiece 16 is optional. The eyepiece 16 is used in those instances where the user wishes to improve the contrast of the image and reduce internal reflections. The eyepiece 16 is selectively removable and is attached to the housing 14 by eyepiece threads 30. The eyepiece threads 30 engage the eyepiece 16 by rotating internal threads of the eyepiece (not shown). The eyepiece threads 30 are 28 mm thread used in camera adaptors and serve the alternate purpose allowing the attaching of the device of the present invention to a camera. A simple ring adapter (such as a 28-37 mm stepping ring) may be employed to connect the device of present invention to a camera.

Also, the retainer ring 24 is threaded and may be rotated to be removed from the housing 14 to access the removal of the spacer 26. Once the retainer ring 24 is removed, the focus dial 28 is rotated until the spacer 26 is unsecured from the housing 14. To re-attach the spacer 26, internal pins (not shown) are aligned on notches and the focus dial 28 is rotated until the spacer pulled back into the housing 14. The retaining ring 24 can then be threaded back onto the housing 14 using retaining threads 34. The selective placement of the spacer 26 allows the device 12 to be used as non-contact dermoscopy device without the spacer, or oil and glass dermoscopy with the spacer extended. With the spacer 26 retracted, the user can effect a dry examination of the skin. With spacer 26 in the extended position, a user can complete a direct contact skin examination, typically employing oil emersion. The sidewalls of the spacer 26 support a glass faceplate. The glass faceplate 22 also incorporates a scale 21 (shown in FIG. 2) to provide the user with information regarding size of a lesion, blood vessel or other object to be viewed.

Figure 4:
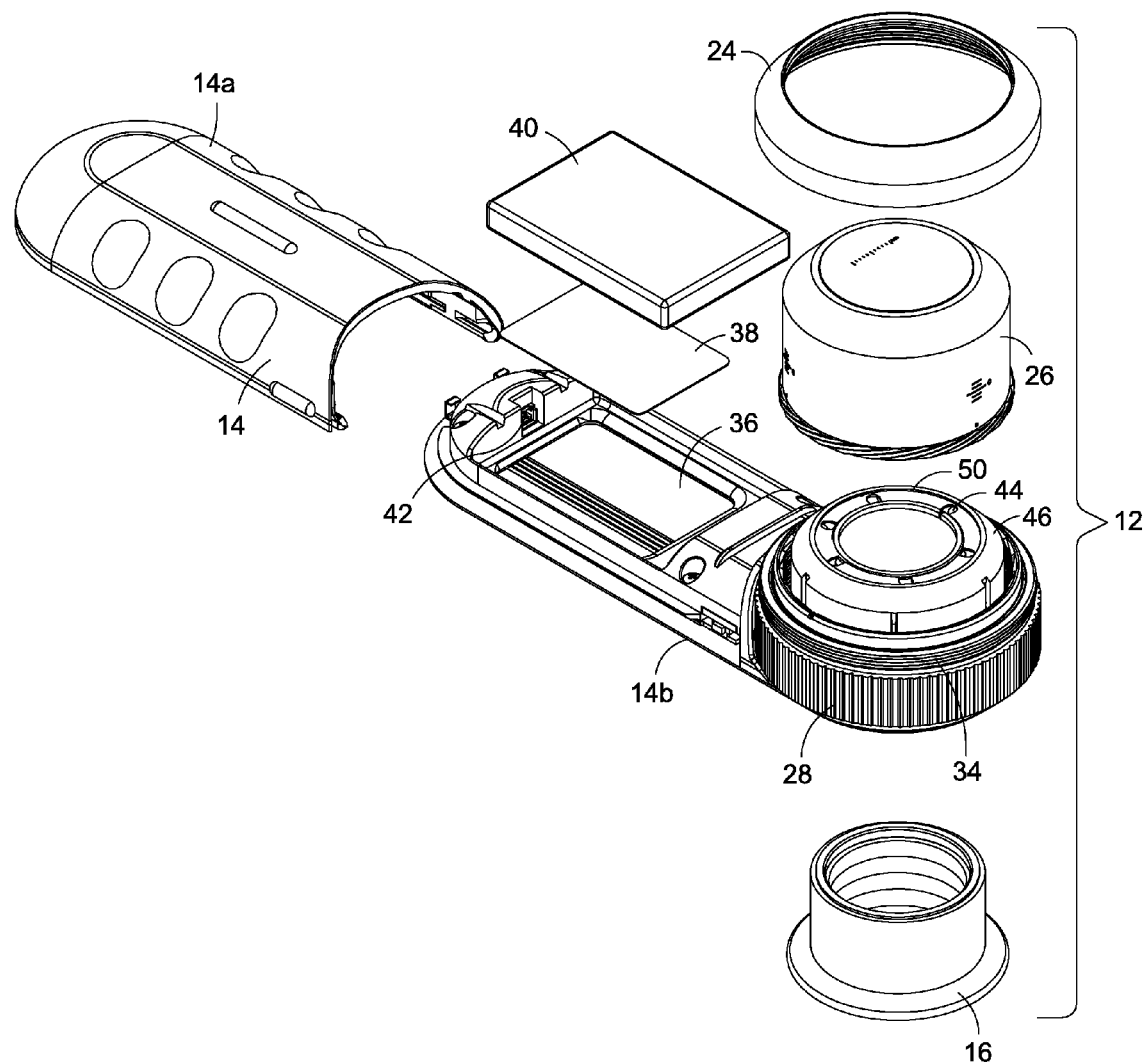
FIG. 4 is an exploded view of device of the present invention demonstrating mechanical sub assembly of the present invention.

Referring particularly to FIG. 4, there is shown an exploded view of the components of the housing 14 of the present invention. The housing 14 is formed from bottom housing component 14a or which can be referred to as a grip, and top housing component 14b also referred to as the mechanical sub-assembly. The bottom housing component 14a interfaces and connects to the top housing component 14a to form the housing 14. The grip 14a provides the primary interface for the user's hand to hold the device 12 during examination. A recess 36 is formed in the top housing component 14b to receive an instruction label 38 and battery 40. The battery 40 nests within the recess 36 and is electrically connected to a power port connector 42 for charging the device 12 and the lighting array 44 for providing a lighting source for the device 12. The battery 40 is selectively removable from the device 12 and the battery 40 provides power to the device 12. The battery 40 is a Lithium rechargeable battery, however it is understood that any like battery power source could be used in relation to the present invention.

The lighting array 44 is housed within a core assembly 46. The core assembly 46 comprises the lighting array 44, a polarizer 50 and lens sub-assembly (not shown) enclosed by a core cover 48. The core assembly 46 nests within the circular structure of the focus dial 28. The lighting array 44 along with the polarizer 50 encircle the forward lens of the device 12 to transmit light upon tissue or object to be viewed.

Figure 5:
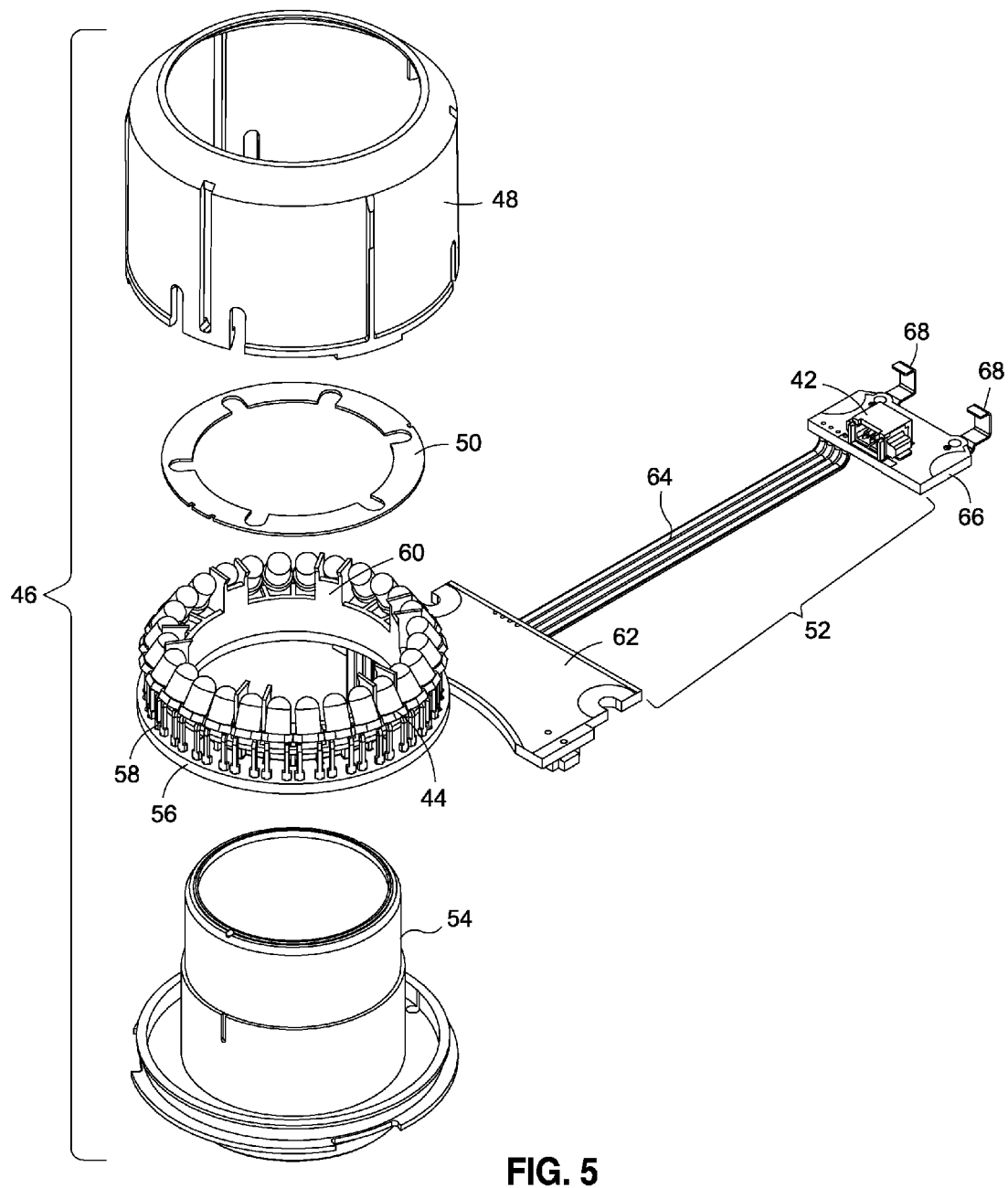
FIG. 5 is an exploded view of the components associated with the LED and lens sub-assemblies along with the PCB assembly of the device of the present invention.

Referring particularly to FIG. 5, there is shown an exploded view of the core assembly 46 along with a printed circuit board ("PCB") assembly 52. With respect to the core assembly 46, as described above, the same comprises lighting array 44, a polarizer 50 and lens sub-assembly enclosed by a core cover 48. The lighting array 44 comprises a circular array of LEDs affixed to a circuit board 56. The circuit board 48 is secured within the housing 14. The LEDs are affixed to and in electrical communication with the circuit board 48 via a plurality of lead lines 58. Each LED has at least two lead lines 58. The LEDs are also supported on the circuit board by a fin 60 which provides support and additionally provides separation between LEDs. The fin 60 additionally provides support for the polarizer 50, the function of which is described in more detail in relation to FIGS. 8-10 below. As can be appreciated each of the components of the core assembly 46 are sized and positioned with a central aperture to permit unobstructed viewing of examined tissues or objects through the lens assembly 54, through the PCB board 56, lighting array 44 and fin 60, polarizer 50 and core cover 48.

The PCB assembly includes the PCB board 56 in electrical communication with the main PCB 62 which houses switching circuitry (not shown). The main PCB interconnects the power port 42 for charging the device 12 to the battery 40 (not shown). Switching circuits on board the main PCB permit the user to selectively activate various combinations of LEDs in the lighting array 44. External switches, discussed more fully below, provide the mechanism for activating and deactivating sets of LEDs. Power lead lines 64 provide electrical connection between the tail PCB 66 and the main PCB 62. The tail PCB 66 includes contacts 66 that interface with a charging station (not shown) for charging a battery (not shown). The power port connection 42 additionally provides a connection to leads 68 as a means for charging the device 12.

Figure 6:
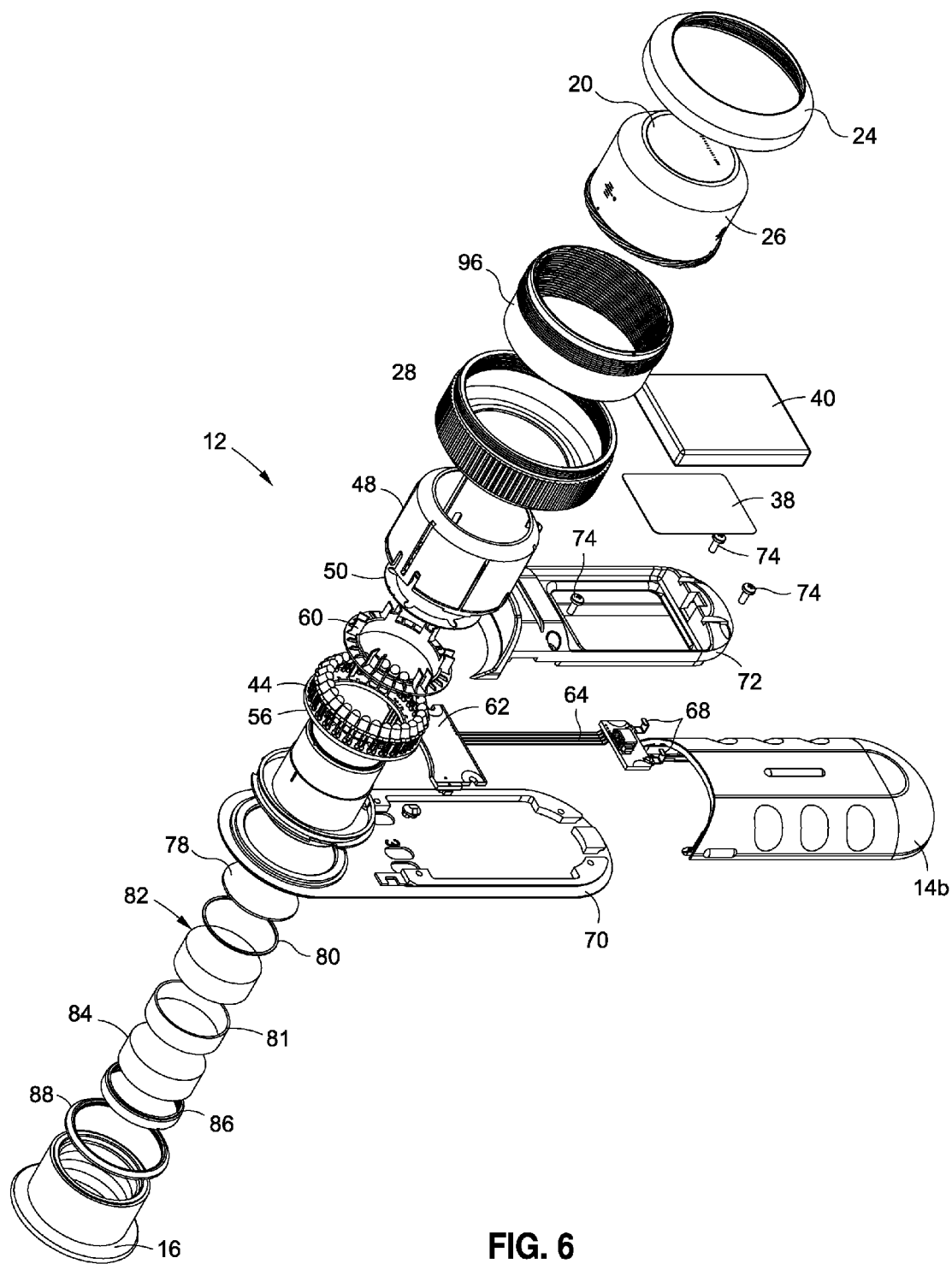
FIG. 6 is an exploded view of the of the various components of the device of the present invention.

Referring specifically to FIG. 6, there is shown an exploded view of the assembled parts of the device 12 of the present invention. The top housing 14b is shown in two assembled parts, the plate 70 and PCB cover 72. Four screws 74 (three shown) provide the fastening means for the plate 72 and PCB cover and main PCB 62 and tail PCB 66.

Lens sub-assembly 54 (shown exploded) comprises a lens tube 76 for enclosing the following: a center polarizer 78 and polarizer spacer 80. The lenses 82 and 84 are dual achromat 25×50 mm lenses. Although the device of the present invention discloses dual achromat lenses other similar lens structures may be utilized such as an aspherical lens, a single convex lens or combination of two or more such lenses or such lenses in combination the double achromat lenses. In addition, the lens may incorporate Hastings lenses. The lenses may also include color tinting. Also included with lenses 82 and 84 is lens spacer 81. The base of the lens sub-assembly 54 is attached to plate 70 by plate ring 88. The focus dial 28 is adapted to engage the helix ring 90 to provide mechanical engagement between the spacer 26 and the focus dial 28 to extend and retract the spacer 26.

Figure 7:
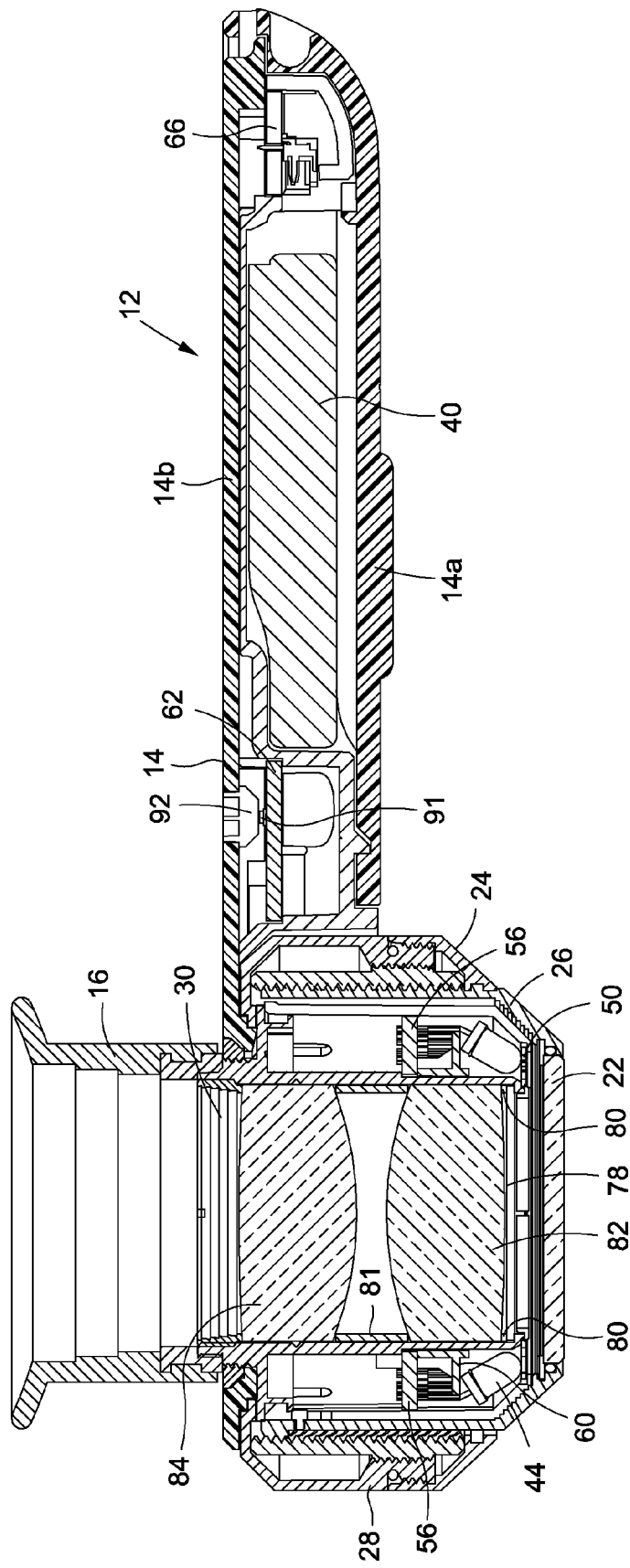
FIG. 7 is a cross sectional view of the device of the present invention.

Referring particularly to FIG. 7, there is shown a cross-sectional view of the device 12 of the present invention. FIG. 7 is useful to demonstrate the cross-sectional view of the viewing corridor through the eyepiece 16 lenses 84 and 82, to enable a user to view objects or tissues with the aid of the LED light. FIG. 7 demonstrates where the spacer 26 is in the retracted position within the housing 14.

The battery 40 is interconnected to the main PCB 62 to provide power to the light array 44. Upon activation of a switch, the light array 44 provides selective lighting through filter 50 on a plurality of the LEDs and unfiltered on a number of other LEDs. The light travels through the glass faceplate 22 to direct light upon examined tissue or an object to be viewed. The lighting array 44 is interconnected to a LED PCB 56 via leads 58. The PCB 56 is in electrical communication with the PCB boards 62 which provide selective activation of the lighting array 44. An indicator LED 91 is interconnected to the main PCB 62 to provide a status indication through indicator LED lens 92 of the device 12 in operation. The LED lens 92 will illuminate to red to indicate that the device 12 is being charged. When the lithium battery 40 is fully charged the indicator LED lens 92 will be green and the device will allow up to two hours of continuous operation or enough power for imaging approximately 600 lesions at 30 seconds per examination. When the battery 40 life reaches less than 25% power remaining, the LED indicator lens 92 will turn orange.

Figure 8:
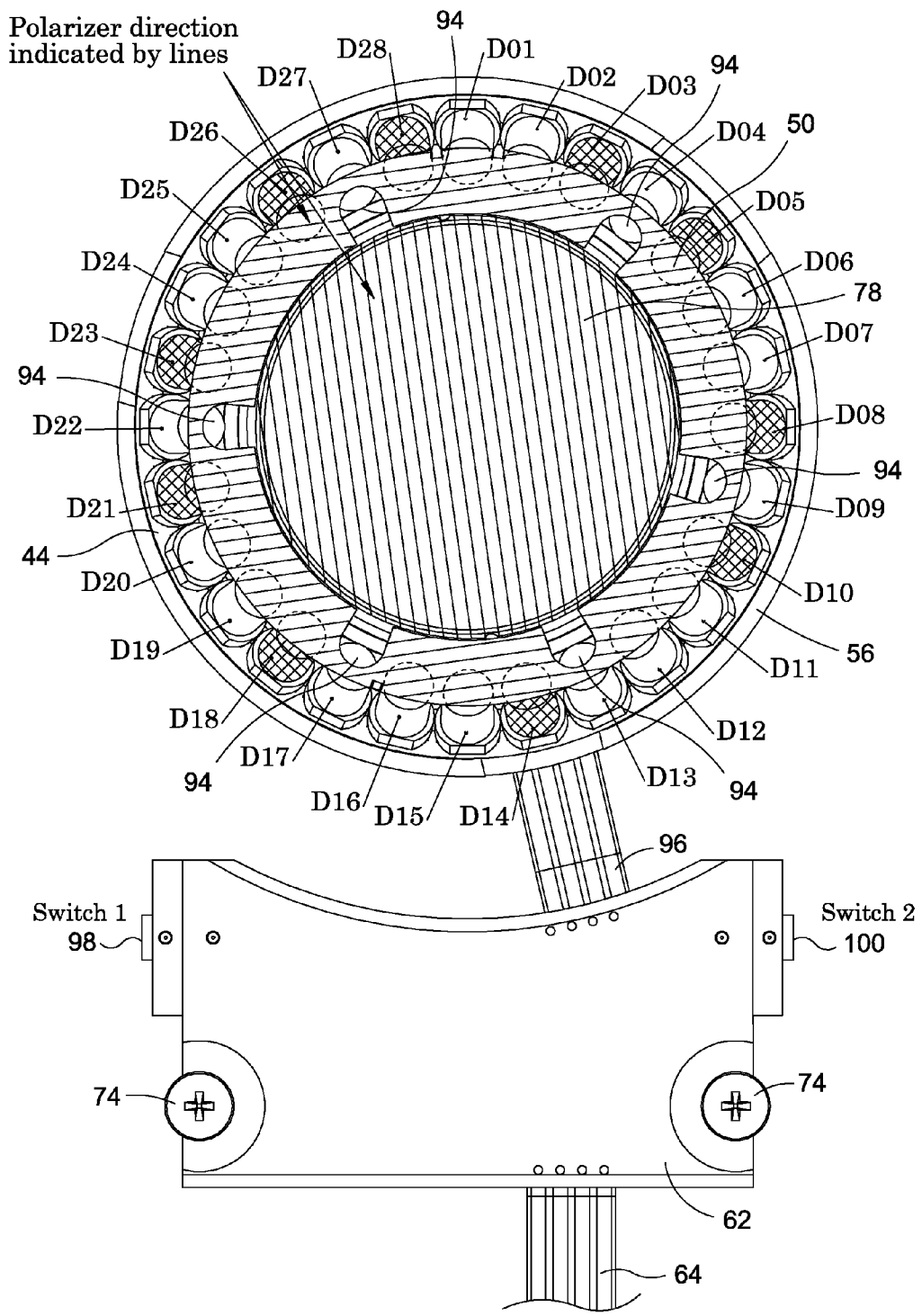
FIG. 8 is an enlarged view of the arrangement of LEDs in the lighting array surrounding the lens structure and in connection with the switching device of the device of the present invention.
Figure 9:
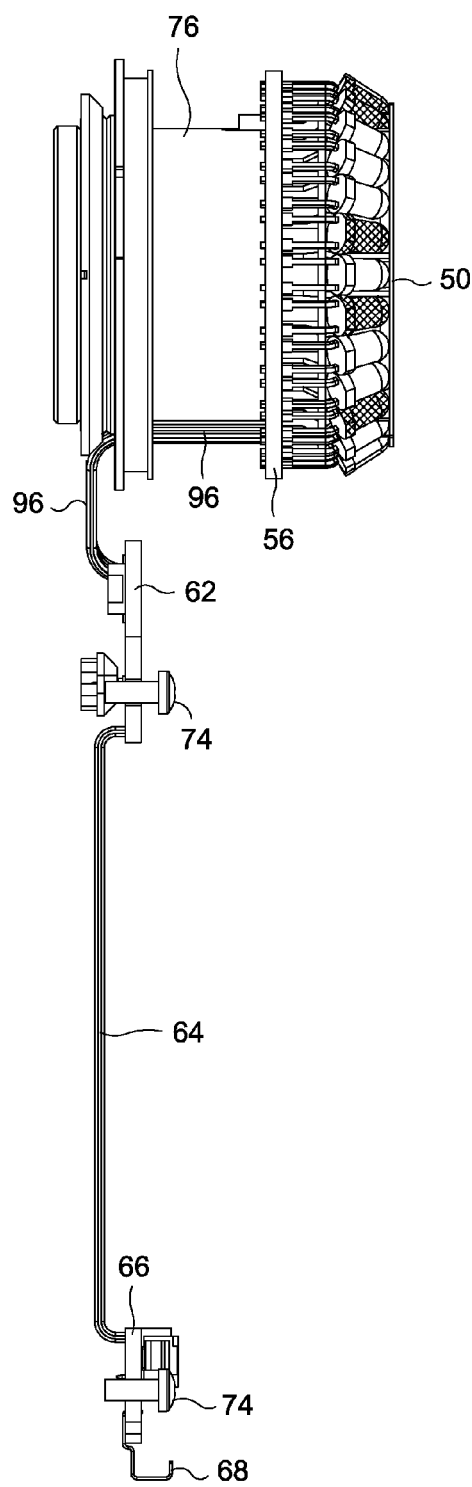
FIG. 9 is a side view of the LED array in combination with the switching circuit and lead lines.
Figure 10:
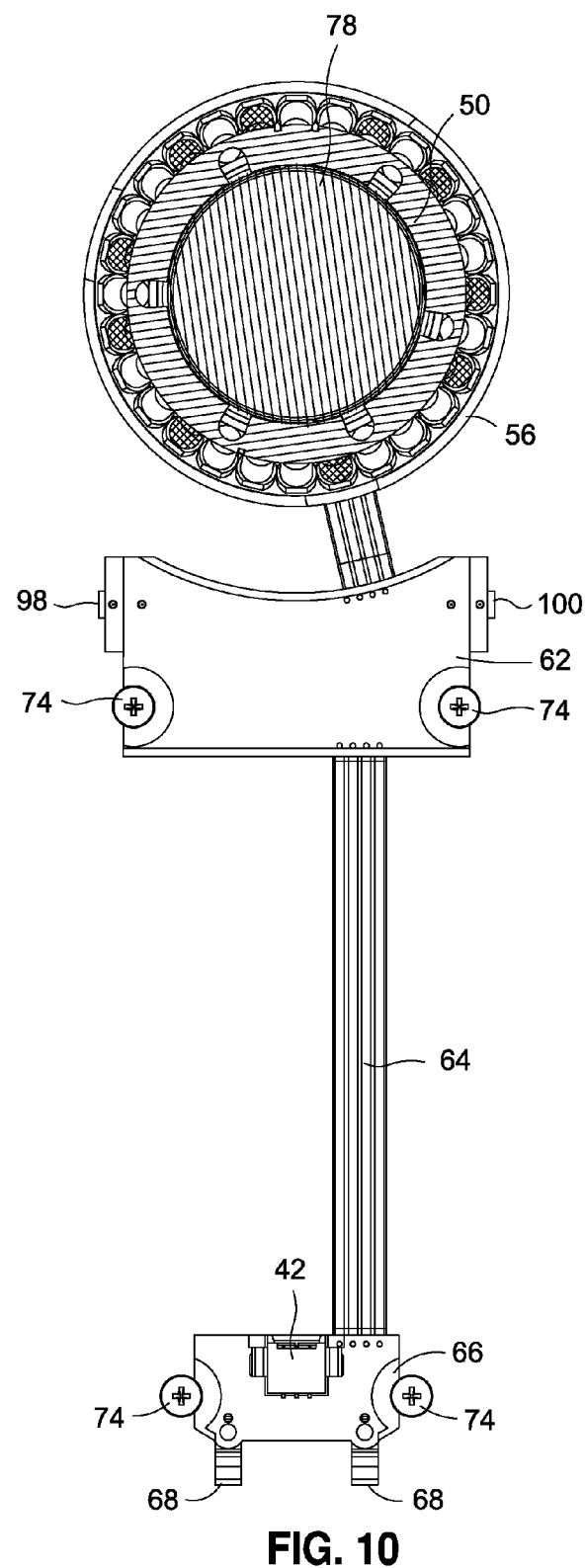
FIG. 10 is a view of the arrangement of LEDs, switching component and tail printed circuit board for interfacing with a recharging jack of the device of the present invention.

Referring collectively to FIGS. 8 through 10, the lighting array 44 and corresponding electronics are shown in greater detail. Referring particularly to FIG. 8, the lighting array 44 is shown wherein 28 LEDs are circumferentially placed about the lens opening through which tissue is viewed for examination. The lens (not shown) is covered by a polarizer 78. As such, all light reflected back from the object surface is filtered through the central polarizer to reach the eye with polarized light through the lenses. The central polarizer aids in diminishing glare from the surface of the skin.

With regard to the lighting array 44 there is shown 28 LEDs of both white LEDs and orange colored LEDs (588 nm). As shown in hatched marking, namely LEDs D03, D05, D08, D10, D14, D18, D21, D23, D26 and D28 represent the orange colored LEDs (588 nm). As such, ten of the LEDs of the LED array 44 are the orange colored (588 nm) LEDs, and the remaining LEDs are white LEDs. The white LEDs comprise D01, D02, D04, D06, D07, D09, D11, D12, D13, D15, D16, D17, D19, D20, D22, D24, D25 and D27. The orange LEDs are SuperBright RL3-Y4545 with the color wave length of 588 nm. Although the present invention discloses the use of an orange LED of 588 nm, it is contemplated by the present invention that such colored LED could range anywhere from 581 nm to 600 nm. The white LEDs of the LED array 44 are Nichia NSPW 310DS.

The LEDs are overlaid with a polarizer 50 which is cross-polarized relative to the central polarizer 78. The polarizer 50 includes a series of openings to expose six of the white LEDs so that when such LEDs are in operation the white light emanating from such LEDs is not polarized by the polarizing filter 50. As such, the light that reflects back from the object to the user's eye is polarized only once by the central polarizer 78. When light emanates from any of the other LEDs of the lighting array 44 the light passes through the light polarizer 50 and such light is polarized 90 degrees opposite of the central polarizer 78. As such, when light from the LEDs that are polarized by polarizer 50 is reflected back from the sample tissue, it is polarizes a second time by the central polarizer 78 causing the light to be crossed polarized when reaching the user's eye. As discussed above, the polarization and cross polarization aids greatly in reducing the glare from the skins surface and allows the user to see more deeply into the skin. Although the lighting array 44 of the device of the present invention 12 includes 28 LEDs, it is contemplated that such device may include any number of LEDs surrounding the central opening for the lens. Furthermore, although the lighting array 44 shows that the LEDs are formed concentrically around the opening, it is contemplated that the LEDs could be staggered or otherwise arranged, the only requirement being that the LEDs provides sufficient light onto the sample tissue, without obstructing the center viewing zone of the device 12. Furthermore, although the device of the present invention discloses 12 filtered white LEDs, six unfiltered white LEDs and ten filtered orange LEDs, it should be understood and contemplated by the present invention that any number of ratios of the types of LEDs disclosed may be utilize and is contemplated by the present invention. Furthermore, the use of non-polarized or non-cross polarized orange LEDs is contemplated.

Referring again particularly to FIGS. 8 through 10, the lighting array 44 is an electrical communication with the main PCB 62 via electrical leads 96. The electrical leads 96 travel from the main PCB 62 up the lens tube 76 to electrically connect to the LED PCB 56. The leads 96 provide both power to the LED as well as on and off signals as directed by the PCB 62 and the device switches described more fully below.

In operation, the LED array 44 is aimed in the direction of the skin, object or lesion to be examined. It is expected that the device be placed approximately 1 inch (25 mm) from the skin. By pushing and holding the power button 98 for approximately one second, the cross-polarized mode will initiate. In this regard, LEDs D01, D02, D06, D07, D11, D12, D15, D16, D19, D20, D24 and D25 will all light providing cross-polarized white light for examination. A further pushing of the button 98 enables the non-polarized mode for viewing the subject tissue without polarize light or for conducting emersion fluid dermoscopy. In this case, non-polarized LEDs D03, D09, D13, D17, D22 and D27 will initiate. A further tap of the button 98 will revert the device back to cross-polarized mode. In either non-polarized or cross-polarized mode, additional illumination may be activated by button 100 which in turn initiates the orange light (588 nm) LEDs. As shown in FIG. 8 that includes LEDs D03, D05, D08, D10, D14, D18, D21, D23, D26 and D28. For reasons discussed above, the orange LEDs provide enhanced viewing of pigmented skin.

For dermoscopy involving skin contact oil immersion or for camera use the focus dial 28 may be utilized for refined focusing by rotating the focus the dial to the left or to the right.

Referring particularly to FIGS. 11-12 there is shown a charging base 200 adapted to receive the device 12. The charging base 200 is connected to a power outlet (not shown) to provide power to charge the on-board battery (not shown) of the device 12. The charging base 200 engages leads 68 (not shown) to provide power to the battery (not show) for charging.

The above description is given by way of example, and not limitation. Given the above disclosure, one skilled in the art could devise variations that are within the scope and spirit of the invention disclosed herein, including various ways of providing orange light in the range of 581 nm to 600 nm to be used in a skin examination lighting device. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An illumination device for non-contact illumination of organic tissue comprising:
 a hand held housing;
 an optical lens incorporated into said housing for providing a magnified view of the tissue;
 a light activation switch;
 a polarizer incorporated into the housing; and
 a light source array comprising a plurality of light emitting diodes incorporated into said housing and in electrical communication with said light activation switch, said light source array comprising;
  a first light circuit for interconnecting a first set of the plurality of light emitting diodes including at least one orange light emitting diode for emitting orange light having a wavelength of between 581 nm and 600 nm, the first light circuit and the polarizer being arranged such that orange light emitted by the first light circuit is polarized;
  a second light circuit for interconnecting a second set of the plurality of light emitting diodes including at least one white light emitting diode for emitting white light, the second light circuit and the polarizer being arranged such that white light emitted by the second light circuit is polarized; and
  a third light circuit for interconnecting a third set of the plurality of light emitting diodes including at least one white light emitting diode for emitting white light, the third light circuit and the polarizer being arranged such that at least a portion of the white light emitted by the third light circuit is not polarized;
 wherein said light source array activation switch is adapted to selectively transition between:
  a first mode wherein the first light circuit and the second light circuit are activated and the third light circuit is deactivated;
  a second mode wherein the first light circuit and the third light circuits are activated and the second light circuit is deactivated;
  a third mode wherein only the second light circuit is activated; and
  a fourth mode wherein only the third light circuit is activated.

2. The illumination device of claim 1 wherein said light source array includes at least one light emitting diode that emits light that is polarized.

3. The illumination device of claim 2 wherein said light source array includes at least one light emitting diode that is not polarized.

4. The illumination device of claim 1 wherein said plurality of light emitting diodes includes at least two white light emitting diodes for every one orange light emitting diode emitting light in the range of 581 nm and 600 nm.

5. The illumination device of claim 4 wherein said at least one orange light emitting diodes emitting light in the range of 581 nm and 600 nm is an orange light emitting diode emitting light at 585 nm.

6. The illumination device of claim 1 wherein said at least one orange light emitting diode has a wavelength of 588 nm.

7. The illumination device of claim 1 wherein said light activation switch is a manual switch.

8. The illumination device of claim 1 wherein said plurality of diodes are formed concentrically around said optical lens.

9. The illumination device of claim 1 wherein said organic tissue is mammalian tissue.

10. The illumination device of claim 1 wherein said organic tissue is human tissue.

11. The illumination device of claim 1 wherein said at least one light source having a wavelength of between 583 nm and 587 nm.

12. The illumination device of claim 1 wherein said at least one light source having a wavelength of between 584 nm and 586 nm.

13. The illumination device of claim 1 wherein said at least one light source having a wavelength of 585 nm.

14. In a hand held dermoscopy illumination device comprising an optical lens for providing a magnified view and an array of light emitting diodes, at least one of said at least one light emitting diodes for emitting non-polarized light and at least one of said light emitting diodes including a polarization filter adjacent thereto to emit polarized light upon an object to be viewed the improvement comprising:
   a light activation switch in electrical communication with said array of light emitting diodes;
   said array including a first light circuit for interconnecting a first set of the plurality of light emitting diodes of the array including at least one orange light emitting diode for emitting orange light, said orange light emitting diode having a wavelength of between 581 nm and 600 nm, the first light circuit and the polarization filter being arranged such that orange light emitted by the first light circuit is polarized; and
   said array including a second light circuit for interconnecting a second set of the plurality of light emitting diodes of the array including at least one white light emitting diode for emitting white light, the second light circuit and the polarization filter being arranged such that white light emitted by the second light circuit is polarized; and
   said array including a third light circuit for interconnecting a third set of the plurality of light emitting diodes including at least one white light emitting diode for emitting white light, the third light circuit and the polarization filter being arranged such that at least a portion of the white light emitting by the third light circuit is not polarized;
   wherein said light activation switch is adapted to selectively transition between:
      a first mode wherein the first light circuit and the second light circuit are activated and the third light circuit is deactivated;
      a second mode wherein the first light circuit and the third light circuits are activated and the second light circuit is deactivated;
      a third mode wherein only the second light circuit is activated; and
      a fourth mode wherein only the third light circuit is activated.

15. The improvement of claim 14 wherein said at least one light emitting diode adapted to emit orange light has a wavelength of 588 nm.

16. The improvement of claim 14 wherein said at least one light emitting diode adapted to emit orange light having a wavelength between 581 nm and 600 is positioned to emit light through said polarizing filter.

17. The improvement of claim 14 wherein said orange light emitting diode having a wavelength of between 583 nm and 587 nm.

18. The improvement of claim 14 wherein said orange light emitting diode having a wavelength of between 584 nm and 586 nm.

19. The improvement of claim 14 wherein said orange light emitting diode having a wavelength of 585 nm.

20. A hand held illumination device for non-contact illumination of organic tissue comprising:
   an optical lens for providing a magnified view of said tissue;
   an array of light emitting diodes, said array comprising:
      at least one orange light emitting diode for emitting orange light, said orange light having a wavelength of between 581 nm and 600 nm; and
      at least one white light emitting diode for emitting white light;
   at least one polarizer for polarizing light emitted from said at least light one orange light emitting diode or said white light emitting diode;
   a switch in electrical communication with said array of light emitting diodes, said switch adapted to provide selective illumination of said at least one orange light emitting diode and said one at least white light emitting diode to enable operation in:
      a first mode wherein only polarized white light is emitted;
      a second mode wherein only non-polarized white light is emitted;
      a third mode wherein only polarized white light and polarized orange light is emitted; and
      a fourth mode wherein only non-polarized white light and polarized orange light is emitted.

21. The device of claim 20 wherein said polarizer polarizes light emitted from said at least one white light emitting diode.

22. The device of claim 20 wherein said array of light emitting diodes comprises at least two white light emitting diodes comprising first and second white light diodes, wherein said polarizer polarizes light emitted from said first white light emitting diode and wherein said second diode is not polarized by said polarizer.

23. The device of claim 20 wherein said orange light emitting diode having a wavelength of between 582 nm and 588 nm.

24. The device of claim 20 wherein said orange light emitting diode having a wavelength of between 583 nm and 587 nm.

25. The device of claim 20 wherein said orange light emitting diode having a wavelength of between 584 nm and 586 nm.

26. The device of claim 20 wherein said orange light emitting diode having a wavelength of 585 nm.

27. The device of claim 20 wherein said orange light emitting diode having a wavelength of 588 nm.

* * * * *